(12) United States Patent
Park et al.

(10) Patent No.: US 9,782,353 B2
(45) Date of Patent: Oct. 10, 2017

(54) FILM COATED TABLET CONTAINING CHOLINE ALFOSCERATE AND PROCESS FOR PREPARING THE SAME

(71) Applicant: DAEWOONG PHARMACEUTICAL CO., LTD., Seongnam-si, Gyeonggi-do (KR)

(72) Inventors: Sang-Han Park, Yongin-si (KR); Hee-Chul Chang, Seoul (KR)

(73) Assignee: DAEWOONG PHARMACEUTICAL CO., LTD., Seongnam-si, Gyeonggi-do (KR)

( * ) Notice: Subject to any disclaimer, the term of this patent is extended or adjusted under 35 U.S.C. 154(b) by 0 days.

(21) Appl. No.: 15/105,048

(22) PCT Filed: Dec. 15, 2014

(86) PCT No.: PCT/KR2014/012320
§ 371 (c)(1),
(2) Date: Jun. 16, 2016

(87) PCT Pub. No.: WO2015/093796
PCT Pub. Date: Jun. 25, 2015

(65) Prior Publication Data
US 2017/0027875 A1    Feb. 2, 2017

(30) Foreign Application Priority Data
Dec. 17, 2013  (KR) .......... 10-2013-0157198

(51) Int. Cl.
*A61K 31/661* (2006.01)
*A61K 33/12* (2006.01)
*A61K 9/28* (2006.01)
*A61K 9/12* (2006.01)
*A61K 9/20* (2006.01)

(52) U.S. Cl.
CPC ............ *A61K 9/2866* (2013.01); *A61K 9/124* (2013.01); *A61K 9/2095* (2013.01); *A61K 9/282* (2013.01); *A61K 31/661* (2013.01); *A61K 33/12* (2013.01)

(58) Field of Classification Search
CPC .... A61K 31/661; A61K 33/12; A61K 9/2095; A61K 9/282; A61K 9/284; A61K 9/2866
See application file for complete search history.

(56) References Cited

U.S. PATENT DOCUMENTS

| 8,633,176 B2 | 1/2014 | Lee et al. | |
| 8,821,928 B2 * | 9/2014 | Hemmingsen | ........ A61K 9/2072 424/457 |
| 2010/0190809 A1 * | 7/2010 | Voorspoels | ............ A61K 9/146 514/272 |
| 2010/0311692 A1 | 12/2010 | Lee et al. | |
| 2011/0082161 A1 * | 4/2011 | Baert | ................... A61K 9/0095 514/272 |
| 2011/0217374 A1 | 9/2011 | Oh et al. | |
| 2014/0100192 A1 | 4/2014 | Lee et al. | |

FOREIGN PATENT DOCUMENTS

| KR | 10-1172699 B1 * | 8/2012 | ............... A61K 9/52 |
| KR | 10-1172699 B1 | 8/2012 | |
| KR | 10-1257919 B1 * | 4/2013 | ............... A61K 9/52 |
| KR | 10-1257919 B1 | 4/2013 | |

OTHER PUBLICATIONS

KR10-1257919B1, published Apr. 30, 2013, translation.*
KR10-1172699B1, published Aug. 9, 2012, translation.*

* cited by examiner

*Primary Examiner* — Audrea Buckley
(74) *Attorney, Agent, or Firm* — Vorys, Sater, Seymour & Pease LLP; Mih Suhn Koh

(57) ABSTRACT

The present invention provides a film coated tablet comprising a first film coating layer comprising hydroxypropyl methylcellulose and a second film coating layer comprising polyvinyl alcohol, on a tablet containing choline alfoscerate as an active ingredient and magnesium aluminometasilicate as an additive; and a process for preparing the same.

16 Claims, 1 Drawing Sheet

FILM COATED TABLET CONTAINING CHOLINE ALFOSCERATE AND PROCESS FOR PREPARING THE SAME

TECHNICAL FIELD

The present invention relates to a film coated tablet containing choline alfoscerate and a process for preparing the same. More specifically, the present invention relates to a film coated tablet obtained by wet-granulating choline alfoscerate having deliquescence along with magnesium aluminometasilicate to form a tablet and then forming double film coating layers with a combination of specific film forming agents on the tablet; and a process for preparing the same.

BACKGROUND ART

Choline alfoscerate, which is an acetylcholine precursor, supplies deficient acetylcholine to restore neurotransmission in the nervous system and repairs damaged nerve cell membranes to normalize neuronal functions. And also, choline alfoscerate normalizes acetylcholine receptor functions in the post-synaptic nerve terminal so as to facilitate neurotransmission, thereby improving the secondary symptoms caused by cerebrovascular defects and the symptoms caused by denatured or degenerative organic brain syndrome. Therefore, choline alfoscerate has been known to be useful for treating senile hypermetamorphosis such as memory impairment, mental derangement, disorientation, and attention deficiency; the change of feeling and behavior such as emotional instability and irritability; senile pseudo-depression and so on. Choline alfoscerate is commercially available in the form of soft capsule, which is orally administered at the dose of 400 mg twice or three times a day.

Meanwhile, choline alfoscerate tends to be dissolved by pulling moisture in from the surrounding air, thereby exhibiting deliquescence and/or hygroscopicity. Therefore, choline alfoscerate is commercially available in the form of soft capsule formulation, which is prepared by filling the liquid phase of choline alfoscerate in soft gelatin capsules. However, in the soft capsule form formulation, choline alfoscerate may move into soft gelatin shells over time. Microorganism deterioration also exists in the soft capsule form formulation. Further, the soft capsule formulation is weak to humidity and heat, which may cause stability problems, e.g., when stored in summer season.

In order to address the deliquescence of choline alfoscerate and the disadvantages of the soft capsule formulation, various researches have been carried out for developing formulations having solid dosage form. For example, Korean Patent Publication No. 10-2009-0088564 discloses a choline alfoscerate-containing pharmaceutical preparation in which choline alfoscerate is adsorbed on colloidal silicone dioxide. Korean Patent No. 10-1172699 discloses a pharmaceutical formulation comprising an adsorption product obtained by adsorbing the choline alfoscerate on magnesium silicate aluminate in a weight ratio of 1:1 to 2:1. And also, Korean Patent No. 10-1257919 discloses a pharmaceutical composition comprising coated particles obtained by coating choline alfoscerate particles with a water soluble polymer such as hydroxypropyl methylcellulose, hydroxypropyl cellulose, polyvinyl alcohol, methacrylic acid copolymers, polyethylene oxide and so on.

However, the prior art formulations require adsorbing the drug itself (i.e., choline alfoscerate) to an excipient (Korean Patent Publication No. 10-2009-0088564, Korean Patent No. 10-1172699) or performing particle-coating processes (Korean Patent No. 10-1257919). In other words, since the prior art formulations require performing adsorption processes or particle-coating processes, the processes for preparing the formulations are complicated and specific equipment (e.g., fluidized bed granulator and so on) is also required. Therefore, the costs for the process are very high and it is difficult to apply to industrial mass production. Furthermore, if a tablet is prepared by using choline alfoscerate adsorbed on colloidal silicon dioxide according to Korean Publication No. 10-2009-0088564, the size of the resulting tablet becomes too large, which results in problem of decreasing patient compliance.

Hence, there is a need to develop a choline alfoscerate-containing tablet which can be prepared according to conventional methods for preparing a tablet without performing additive-adsorption and/or particle-coating. And also, there is a need to develop a choline alfoscerate-containing tablet which can prevent deliquescence and hygroscopicity of choline alfoscerate and exhibit equivalent dissolution pattern to the commercially available soft capsule formulation.

DISCLOSURE

Technical Problem

The present inventors performed extensive researches for various pharmaceutically compatible additives which make it possible to employ conventional methods for preparing a tablet and various film forming agents which can prevent deliquescence of choline alfoscerate. As a result, the present inventors found that, when a film coated tablet is prepared by forming a tablet according to a conventional wet-granulation method using magnesium aluminometasilicate (one of porous materials) in a small amount and then forming a film coating layer with a combination of specific film forming agents (i.e., hydroxypropyl methylcellulose and polyvinyl alcohol), conventional methods for preparing a tablet are applicable and deliquescence of choline alfoscerate can be prevented. Further, the resulting film coated tablet can be formulated to exhibit equivalent dissolution pattern to the commercially available soft capsule formulation.

Therefore, it is an object of the present invention to provide a film coated tablet containing choline alfoscerate as an active ingredient and a process for preparing the same.

Technical Solution

In accordance with an aspect of the present invention, there is provided a film coated tablet comprising a first film coating layer comprising hydroxypropyl methylcellulose and a second film coating layer comprising polyvinyl alcohol, on a tablet containing choline alfoscerate as an active ingredient and magnesium aluminometasilicate as an additive.

In accordance with another aspect of the present invention, there is provided a process for preparing a film coated tablet comprising: (a) wet-granulating a mixture of choline alfoscerate, magnesium aluminometasilicate, and a pharmaceutically acceptable excipient, (b) mixing the granules obtained in step (a) with a pharmaceutically acceptable excipient, followed by compressing to form a tablet, (c) forming a first film coating layer comprising hydroxypropyl methylcellulose on the tablet obtained in step (b), and (d) forming a second film coating layer comprising polyvinyl alcohol on the film coating layer obtained in step (c).

Advantageous Effects

The choline alfoscerate-containing tablet according to the present invention, which is formulated using magnesium aluminometasilicate (one of porous materials) along with a combination of specific film forming agents, can effectively prevent deliquescence and hygroscopicity of choline alfoscerate. And also the tablet of the present invention can be formulated to exhibit equivalent dissolution pattern to the commercially available soft capsule formulation. Especially, the choline alfoscerate-containing tablet according to the present invention can be prepared according to conventional methods for preparing a tablet (e.g., wet-granulation methods) without performing additive-adsorption and/or particle-coating. Therefore the process the same is simple, needs no special equipment, can be performed with low cost, and is suitable for industrial mass production. Furthermore, the tablet of the present invention can be prepared by using the additive (i.e., magnesium aluminometasilicate) in a small amount, according to conventional methods for preparing a tablet. Therefore, there is less restriction on the amount of excipients such as disintegrant, lubricant, and the like for obtaining a desired dissolution pattern, which makes it possible to prepare a tablet having a size suitable for patients' taking.

BEST MODE

Figure 1:
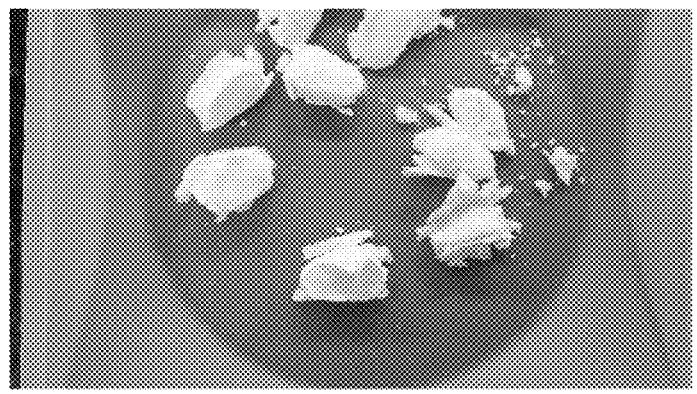
FIG. 1 shows the appearances of the film coated tablets obtained by forming a film coating layer with hydroxypropyl methylcellulose, the tablets of which were stored at room temperature condition (i.e., the condition of 25° C., 60% relative humidity) for 72 hours.

The present invention provides a film coated tablet comprising a first film coating layer comprising hydroxypropyl methylcellulose and a second film coating layer comprising polyvinyl alcohol, on a tablet containing choline alfoscerate as an active ingredient and magnesium aluminometasilicate as an additive.

In the film coated tablet according to the present invention, the active ingredient (i.e., choline alfoscerate) may be used in a therapeutically effective amount, for example in an amount of 200 mg, 400 mg and so on per 1 tablet, but not limited thereto.

The uncoated tablet used in the present invention includes magnesium aluminometasilicate as one of the additives. Magnesium aluminometasilicate, which is a pharmaceutically compatible additive with choline alfoscerate, enables the tablet-preparation according to conventional methods for preparing a tablet such as wet-granulation methods, as described below. Magnesium aluminometasilicate is a white powder having chemical formula $Al_2O_2 \cdot 2Mg \cdot 3O_3Si$, and also referred to as Silodrate or Simaldrate. It is water-insoluble and has hygroscopicity under the condition of relative humidity of not less than 70%. In addition, commercially available Neusilin™ (Fuji Chemical Industry) may be used.

The magnesium aluminometasilicate may be used in an amount of preferably 0.35 to 0.45 part by weight, more preferably 0.4 to 0.43 part by weight, most preferably about 0.425 part by weight, based on 1 part by weight of the choline alfoscerate. When magnesium aluminometasilicate is used in an amount of not more than 0.3 part by weight based on 1 part by weight of the choline alfoscerate, sticking problems may occur during the compression. In addition, when magnesium aluminometasilicate is used in an amount of not less than 0.5 part by weight based on 1 part by weight of the choline alfoscerate, the bulk-density of the resulting granules gets very low. Thus, since significant amounts of the granules escape from a compression die during the compression, it may be difficult to prepare tablets with desired weight.

The film coated tablet according to the present invention includes a first film coating layer comprising hydroxypropyl methylcellulose and a second film coating layer comprising polyvinyl alcohol. The hydroxypropyl methylcellulose in the first film coating layer may be present in an amount of preferably 0.02 to 0.1 part by weight, more preferably 0.03 to 0.05 part by weight, based on 1 part by weight of the choline alfoscerate. The polyvinyl alcohol in the second film coating layer may be present in an amount of preferably 0.02 to 0.2 part by weight, more preferably 0.04 to 0.07 part by weight, based on 1 part by weight of the choline alfoscerate.

The present invention also provides a process for preparing the film coated tablet. In other words, the present invention provides a process for preparing a film coated tablet comprising: (a) wet-granulating a mixture of choline alfoscerate, magnesium aluminometasilicate, and a pharmaceutically acceptable excipient, (b) mixing the granules obtained in step (a) with a pharmaceutically acceptable excipient, followed by compressing to form a tablet, (c) forming a first film coating layer comprising hydroxypropyl methylcellulose on the tablet obtained in step (b), and (d) forming a second film coating layer comprising polyvinyl alcohol on the film coating layer obtained in step (c).

In the process according to the present invention, the magnesium aluminometasilicate in the mixture of step (a) may be used in an amount of preferably 0.35 to 0.45 part by weight, more preferably 0.4 to 0.43 part by weight, most preferably about 0.425 part by weight, based on 1 part by weight of the choline alfoscerate. The mixture in step (a) may further comprise an additive conventionally used in the preparation of granules, for example, low substituted hydroxypropyl cellulose, and microcrystalline cellulose, etc., but not limited thereto. In an embodiment, the mixture of step (a) may consist of 0.35 to 0.45 part by weight of magnesium aluminometasilicate, 0.01 to 0.04 part by weight of low substituted hydroxypropyl cellulose, and 0.1 to 0.4 part by weight of microcrystalline cellulose, based on 1 part by weight of the choline alfoscerate. In another embodiment, the mixture of step (a) may consist of 400 mg of choline alfoscerate, 170 mg of magnesium aluminometasilicate, 10 mg of low substituted hydroxypropyl cellulose, and 25 mg of microcrystalline cellulose, per 1 tablet of the film coated tablet.

The wet granulation of step (a) may be carried out by using a granulator conventionally used in the art, e.g., a high-shear mixer. The wet granulation may be carried out by using either only a kneading solvent (e.g., water, ethanol, or a mixture of water and ethanol) or a binder solution obtained by dissolving a binder in a solvent. In an embodiment, the wet-granulation of step (a) may be carried out by using a hydroxypropyl cellulose solution as a binder solution. For example, the binder solution may be obtained by dissolving hydroxypropyl cellulose in water or a mixed solvent of water and ethanol. The hydroxypropyl cellulose used as a binder may be used in an amount ranging from 0.05 to 0.08 part by weight based on 1 part by weight of the choline alfoscerate. In an embodiment, about 25 mg of hydroxypropyl cellulose may be used as a binder, based on 400 mg of choline alfoscerate. The obtained granules (i.e., wet granules) may be dried by using a conventional dryer, such as a hot-water circulating dryer or a fluidized bed dryer. Preferably, the resulting granules have water content ranging from 1.0 weight % to 2.0 weight %. If necessary, a sifting step may be also carried out to obtain granules having uniform size distribution.

Step (b) is carried out by mixing the granules obtained in step (a) with a pharmaceutically acceptable excipient, followed by compressing to form a tablet. The pharmaceutically acceptable excipient of step (b) comprises a disintegrant selected from the group consisting of silicified microcrystalline cellulose (Prosolv™), croscarmellose sodium, sodium starch glycolate, and crospovidone, an additive selected from the group consisting of microcrystalline cellulose, lactose, and mannitol, and a lubricant selected from the group consisting of magnesium stearate, calcium stearate, and talc, but not limited thereto. The excipients (such as disintegrant, additive) and the amount thereof may be adequately adjusted to exhibit equivalent dissolution pattern to the commercially available soft capsule formulation.

Step (c) is carried out by forming a first film coating layer comprising hydroxypropyl methylcellulose on the tablet obtained in step (b). The hydroxypropyl methylcellulose of step (c) may be used in an amount of preferably 0.02 to 0.1 part by weight, more preferably 0.03 to 0.05 part by weight, based on 1 part by weight of the choline alfoscerate. And also, a commercially available hydroxypropyl methylcellulose-based hydrophilic matrix system (e.g., Opadray™ 03B28796 (Colorcon, Inc, USA)) may be used for the hydroxypropyl methylcellulose to form a first film coating layer. The hydroxypropyl methylcellulose-film coating may be carried out according to an organic coating method conventionally used in the field of pharmaceutics. In an embodiment, step (c) is carried out by coating the tablet obtained in step (b) with a film coating solution obtained by dissolving hydroxypropyl methylcellulose (or Opadray™ 03B28796) in a mixed solvent of anhydrous ethanol and methylene chloride.

Step (d) is carried out by forming a second film coating layer comprising polyvinyl alcohol on the film coating layer obtained in step (c). The polyvinyl alcohol may be used in an amount of preferably 0.02 to 0.2 part by weight, more preferably 0.04 to 0.07 part by weight, based on 1 part by weight of the choline alfoscerate. And also, a commercially available poly(vinyl alcohol)-based film forming agent (e.g., Opadray™ Yellow 85F92177 (Colorcon, Inc, USA)) may be used for the polyvinyl alcohol to form a second film coating layer. The polyvinyl alcohol-film coating may be carried out according to an organic coating method or an aqueous coating method. It has been found by the present invention that the polyvinyl alcohol-film coating can be carried out according to an aqueous coating method which is eco-friendly and enables ensuring great safety. In an embodiment, step (d) may be carried out by coating the film coated tablet obtained in step (c) with a film coating solution obtained by dissolving polyvinyl alcohol (or Opadray™ Yellow 85F92177) in water (e.g., purified water).

If necessary, the process according to the present invention may further comprise forming an additional film coating layer (a third film coating layer) to improve polishing property. Opadray™ 97W19196 (Colorcon, Inc, USA) may be used as a coating agent to form a third film coating layer, but not limited thereto. Forming a third film coating layer may be carried out by using a coating solution prepared by dissolving Opadray™ 97W19196 in purified water.

The present invention will be described in further detail with reference to the following examples. These examples are for illustrative purposes only and are not intended to limit the scope of the present invention.

Example 1

Selection and Evaluation of Additives

Various excipients were studied in order to select pharmaceutically compatible additives with choline alfoscerate, which make it possible to prepare a tablet according to a conventional method for preparing a tablet. Briefly, preliminary tests were performed by preparing choline alfoscerate-containing tablets with various excipients through wet granulation method and then evaluating the respective compressibility thereof. From the results of the preliminary tests, it was identified that magnesium aluminometasilicate showed relatively excellent compressibility. Additional studies were carried out on the tablets prepared with various contents as presented in the following table 1.

In other words, choline alfoscerate, magnesium aluminometasilicate, low substituted hydroxypropyl cellulose, and microcrystalline cellulose were sieved with 24 mesh and then mixed each other. A binder solution was prepared by dissolving hydroxypropyl cellulose in a mixed solvent of purified water and ethanol. The binder solution was added to the mixture in a high shear mixer to form wet granules, which was then dried using a fluidized bed dryer. The obtained granules were sifted with 24 mesh, mixed with silicified microcrystalline cellulose (Prosolv™), croscarmellose sodium, microcrystalline cellulose, and magnesium stearate, and then compressed to form a tablet having about 20 kp of hardness.

TABLE 1

| Components (mg/tablet) | Example 1-1 | Example 1-2 | Example 1-3 |
|---|---|---|---|
| Choline alfoscerate | 400 | 400 | 400 |
| Magnesium aluminometasilicate | 170 | 120 | 200 |
| Low substituted hydroxypropyl cellulose | 10 | 10 | 10 |
| Microcrystalline cellulose (added when granulating) | 100 | 100 | 100 |
| Hydroxypropyl cellulose | 25 | 25 | 25 |
| Purified water | 25 | 25 | 25 |
| Anhydrous ethanol | 250 | 250 | 250 |
| Prosolv | 15 | 15 | 15 |
| Croscarmellose sodium | 33 | 33 | 33 |
| Microcrystalline cellulose (added when compressing) | 55 | 55 | 55 |
| Magnesium stearate | 7 | 7 | 7 |
| Total weight (mg/tablet) | 815 | 765 | 845 |

All of the tablets prepared in Example 1-1 to 1-3 showed appropriate hardness ranges and dissolution patterns. However, the tablet of Example 1-2 exhibits sticking problems during the compression. The tablet of Example 1-3 showed too low bulk-density to prepare tablets with desired weight, because significant amounts of the granules escaped from the compression die during the compression. Therefore, it can be seen that magnesium aluminometasilicate is used in an amount of preferably 0.35 to 0.45 part by weight, more preferably 0.4 to 0.43 part by weight, most preferably about 0.425 part by weight, based on 1 part by weight of the choline alfoscerate.

Example 2

Selection and Evaluation of Coating Agents

When the tablets of Example 1-1 to 1-3 were stored at the condition of 25° C., 60% relative humidity, all the tablets showed deteriorated appearances such as moisture-adsorption on the tablet surface (i.e., deliquescence and/or hygroscopicity). In order to evaluate potential inhibition against deliquescence/hygroscopicity, suitability was evaluated on various film coating agents. Any appearance change of the resulting film coated tablets was evaluated and the possibility for employing an aqueous coating method which is eco-friendly and enables ensuring great safety was also evaluated.

(1) Evaluation on Hydroxypropyl Methylcellulose-Film Coating

Hydroxypropyl methylcellulose-film coating was employed using water as a solvent. However, the tablet surface was dissolved upon directly contacting with water, which makes it impossible to proceed with the aqueous coating. Therefore, a film coating layer comprising hydroxypropyl methylcellulose was formed on the tablet obtained in Example 1-1 through an organic coating method, according to the components and contents shown in the following table 2. In other words, the film coated tablet was prepared by dissolving the hydroxypropyl methylcellulose-based coating agent (Opadray™ 03B28796 (Colorcon, Inc, USA)) in a mixed solvent of anhydrous ethanol and methylene chloride to obtain a coating solution and then film-coating with the coating solution to form a film coating layer on the tablet obtained in Example 1-1.

TABLE 2

| Components (mg) | Example 2-1 |
|---|---|
| Opadray ™ 03B28796 | 15 |
| Anhydrous ethanol | 75 |
| Methylene chloride | 75 |
| Total coating amount (mg) | 15 |

When the resulting film coated tablet was stored at room temperature condition (the condition of 25° C., 60% relative humidity), the appearance thereof was deteriorated after about 8 hours (FIG. 1). When the resulting film coated tablet was stored at accelerated condition (the condition of 40° C., 75% relative humidity), the appearance thereof was deteriorated in less than 1 hour (see Tables 5 and 6 below).

(2) Evaluation on Polyvinyl Alcohol-Film Coating

Polyvinyl alcohol-film coating was employed using water as a solvent. However, the tablet surface was dissolved upon directly contacting with water, which makes it impossible to proceed with the aqueous coating. Therefore, a film coating layer comprising polyvinyl alcohol was formed on the tablet obtained in Example 1-1 through an organic coating method, according to the components and contents shown in the following table 3. In other words, the film coated tablet was prepared by dissolving the poly(vinyl alcohol)-based coating agent (Opadray™ Yellow 85F92177 (Colorcon, Inc, USA)) in a mixed solvent of anhydrous ethanol and methylene chloride to obtain a coating solution and then film-coating with the coating solution to form a film coating layer on the tablet obtained in Example 1-1.

TABLE 3

| Components (mg) | Example 2-2 |
|---|---|
| Opadray ™ Yellow 85F92177 | 25 |
| Anhydrous ethanol | 125 |
| Methylene chloride | 125 |
| Total coating amount (mg) | 25 |

Figure 2:
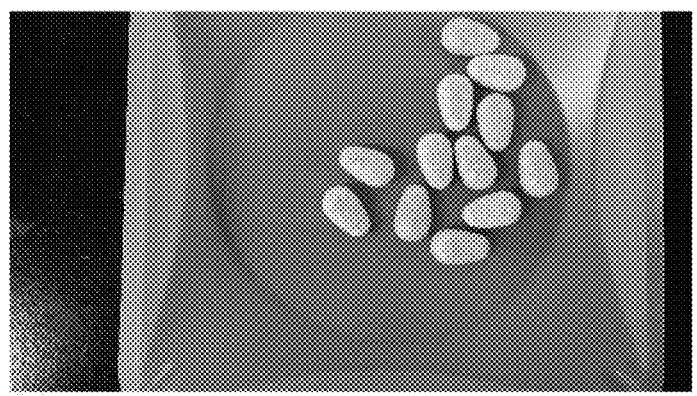
FIG. 2 shows the appearances of the film coated tablets obtained by forming a film coating layer with polyvinyl alcohol.

The resulting film coated tablet exhibited inappropriate appearances having powders stuck on the surface of the tablet (FIG. 2). When the resulting film coated tablet was stored at room temperature condition (the condition of 25° C., 60% relative humidity) and at accelerated condition (the condition of 40° C., 75% relative humidity), the appearances thereof were deteriorated greater than the hydroxypropyl methylcellulose-based coating agent-containing film coated tablet (see Tables 5 and 6 below). In other words, the polyvinyl alcohol-based coating agent was not appropriate for employing an organic coating method.

(3) Evaluation of Two Layer-Film Coating

Both a film coating layer comprising hydroxypropyl methylcellulose and a film coating layer comprising polyvinyl alcohol were formed on the tablet obtained in Example 1-1, according to the components and contents shown in the following Table 4. In other words, the film coated tablet having a first film coating layer was prepared by dissolving Opadray™ 03B28796 (Colorcon, Inc, USA) in a mixed solvent of anhydrous ethanol and methylene chloride to obtain a first coating solution and then film-coating with the first coating solution to form a film coating layer on the tablet obtained in Example 1-1. Subsequently, the film coated tablet having two coating layers was prepared by dissolving Opadray™ Yellow 85F92177 (Colorcon, Inc, USA) in purified water to obtain a second coating solution and then film-coating with the second coating solution to additionally form a film coating layer on the tablet having the first film coating layer.

TABLE 4

| | Components (mg) | Example 2-3 |
|---|---|---|
| First film coating layer | Opadray ™ 03B28796 | 15 |
| | Anhydrous ethanol | 75 |
| | Methylene chloride | 75 |
| Second film coating layer | Opadray ™ Yellow 85F92177 | 25 |
| | Purified water | 166.67 |
| Total coating amount (mg) | | 40 |

The tablet of Example 1-1 (uncoated tablet) and the resulting film coated tablets in the above (Example 2-1 to 2-3) were exposed to air at room temperature condition (the condition of 25° C., 60% relative humidity) or at accelerated condition (the condition of 40° C., 75% relative humidity). The appearance changes are presented in the following tables 5 and 6.

TABLE 5

Storage at the condition of 25° C., 60% relative humidity

|  | Example 1-1 | Example 2-1 | Example 2-2 | Example 2-3 |
|---|---|---|---|---|
| After 6 hours | ○ | ○ | ○ | ○ |
| After 12 hours | ○ | X | X | ○ |
| After 18 hours | X | X | X | ○ |
| After 24 hours | X | X | X | ○ |
| After 48 hours | X | X | X | ○ |
| After 72 hours | X | X | X | ○ |

○: no significant change of appearance,
X: significant change of appearance

TABLE 6

Storage at the condition of 40° C., 75% relative humidity

|  | Example 1-3 | Example 2-1 | Example 2-2 | Example 2-3 |
|---|---|---|---|---|
| After 1 hour | X | X | X | ○ |
| After 2 hours | X | X | X | ○ |
| After 3 hours | X | X | X | ○ |
| After 4 hours | X | X | X | ○ |
| After 5 hours | X | X | X | X |

○: no significant change of appearance,
X: significant change of appearance

Figure 3:
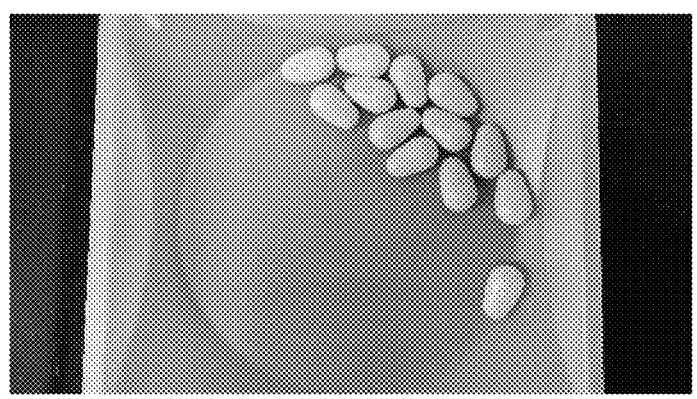
FIG. 3 shows the appearances of the film coated tablets obtained according to the present invention [i.e., the film coated tablets having both a film coating layer comprising hydroxypropyl methylcellulose and a film coating layer comprising polyvinyl alcohol (Example 2-3)], the tablets of which were stored at room temperature condition (i.e., the condition of 25° C., 60% relative humidity) for 72 hours.

The uncoated tablet (Example 1-1) showed no appearance change up to 6 hours to 12 hours when stored at room temperature condition. In contrast, the film coated tablet containing only a HPMC-based coating agent (Example 2-1) and the film coated tablet containing only a PVA-based coating agent (Example 2-2) showed the stabilities similar to the uncoated tablet, when stored at room temperature condition. However, the film coated tablet having two coating layers according to the present invention (Example 2-3) maintained favorable appearance even after 72 hours (FIG. 3). And also, when stored at accelerated condition, all the tablets except for the film coated tablet having two coating layers according to the present invention (Example 2-3) showed significant appearance changes. Especially, it can be seen that the coating methods of the present invention as in Example 2-3 makes it possible to form a PVA coating layer (which requires employing an aqueous coating method) for improving the stability of the tablet, in spite of deliquescence and hygroscopicity of the active ingredient (choline alfoscerate).

Example 3

Comparative Dissolution Test

According to the components and contents presented in Table 7 below, an additional film coating layer was formed on the film coated tablet obtained in Example 2-3 in order to improve polishing property. In other words, the film coated tablet having two coating layers (i.e., tablet of Example 3-1) was prepared by dissolving Opadray™ 97W19196 (Colorcon, Inc, USA) in purified water to obtain a third coating solution and then film-coating with the third coating solution to additionally form a film coating layer on the tablet obtained in Example 2-3. The components and contents of each film coating layer of Example 3-1 are presented in Table 7.

TABLE 7

|  | Components (mg) | Example 3-1 |
|---|---|---|
| First film coating layer | Opadray ™ Clear 03K19229 | 15 |
|  | Anhydrous ethanol | 75 |
|  | Methylene chloride | 75 |
| Second film coating layer | Opadray ™Yellow 85F92177 | 25 |
|  | Purified water | 166.67 |
| Third film coating layer | Opadry ™ 97W19196 | 1 |
|  | Purified water | 14.28 |
| Total coating amount (mg) |  | 41 |

Comparative dissolution tests were performed on the uncoated tablets of Example 1-1 (n=6), the film coated tablets of Example 3-1 (n=6) and the commercially available soft capsule formulation [Gliatilin Soft Capsule (Daewoong Pharmaceutical Co., Ltd), choline alfoscerate 400 mg, Comparative Example) (n=6). Purified water was used as a dissolution medium and the dissolution tests were performed at 37° C. and at the paddle rotation speed of 50 rpm. An aliquot was taken from the dissolution medium at the time of 15, 20, 30, 45, and 60 minutes, followed by filtering for analysis. Separately, 22 mg of choline alfoscerate (reference standard) was added to a 100 ml volumetric flask and a mixed solution of water and acetonitrile (1:1, v/v) was added thereto (up to the mark of the volumetric flask) to prepare a standard solution. Each aliquot was analyzed with HPLC under the following conditions.

<HPLC Analysis Condition>
Column: Inertsil $NH_2$ Column
Mobile phase: Water:Acetonitrile=40:60 (v/v)
Detector: Refractive Index Detector
Flow rate: 1.5 ml/min
Injection volume: 50 ul The results of the comparative dissolution tests are shown in Table 8 below.

TABLE 8

Comparative dissolution test

|  | Dissolution rate (%) | | |
|---|---|---|---|
|  | Example 1-1 | Example 3-1 | Comparative Example |
| 15 minutes | 94.36 | 95.96 | 100.2 |
| 20 minutes | 100.88 | 99.35 | 101.36 |
| 30 minutes | 100.80 | 101.87 | 102.11 |
| 45 minutes | 100.75 | 102.29 | 102.08 |
| 60 minutes | 101.17 | 102.25 | 102.15 |

Comparative Example (soft capsule) showed immediate drug release of more than 100% at the time of 15 minutes. The two test formulations (i.e., Examples 1-1 and 3-1) also showed immediate drug release profiles in 15 minutes. From the results of Table 8, it can be seen that both of the uncoated tablet of Example 1-1 and the film coated tablet of Example 3-1 show equivalent dissolution patterns to the comparative example (i.e., the commercially available soft capsule formulation), without exhibiting significant difference in drug release profile.

The invention claimed is:
1. A film coated tablet comprising:
a first film coating layer comprising hydroxypropyl methylcellulose, and
a second film coating layer comprising polyvinyl alcohol, wherein the tablet contains an active ingredient of choline alfoscerate and an additive of magnesium aluminometasilicate.

2. The film coated tablet according to claim 1, wherein the magnesium aluminometasilicate is present in an amount of 0.35 to 0.45 part by weight based on 1 part by weight of the choline alfoscerate.

3. The film coated tablet according to claim 1, wherein the hydroxypropyl methylcellulose in the first film coating layer is present in an amount of 0.02 to 0.1 part by weight based on 1 part by weight of the choline alfoscerate.

4. The film coated tablet according to claim 1, wherein the polyvinyl alcohol in the second film coating layer is present in an amount of 0.02 to 0.2 part by weight based on 1 part by weight of the choline alfoscerate.

5. A process for preparing a film coated tablet comprising:
(a) wet-granulating a mixture of choline alfoscerate, magnesium aluminometasilicate, and a pharmaceutically acceptable excipient,
(b) mixing the granules obtained in step (a) with a pharmaceutically acceptable excipient, followed by compressing to form a tablet,
(c) forming a first film coating layer comprising hydroxypropyl methylcellulose on the tablet obtained in step (b), and
(d) forming a second film coating layer comprising polyvinyl alcohol on the film coating layer obtained in step (c).

6. The process according to claim 5, wherein the magnesium aluminometasilicate in the mixture of step (a) is present in an amount of 0.35 to 0.45 part by weight based on 1 part by weight of the choline alfoscerate.

7. The process according to claim 5, wherein the mixture of step (a) consists of 0.35 to 0.45 part by weight of magnesium aluminometasilicate, 0.01 to 0.04 part by weight of low substituted hydroxypropyl cellulose, and 0.1 to 0.4 part by weight of microcrystalline cellulose, based on 1 part by weight of the choline alfoscerate.

8. The process according to claim 7, wherein the mixture of step (a) consists of 400 mg of choline alfoscerate, 170 mg of magnesium aluminometasilicate, 10 mg of low substituted hydroxypropyl cellulose, and 25 mg of microcrystalline cellulose, per 1 tablet of the film coated tablet.

9. The process according to claim 5, wherein the wet-granulation of step (a) is carried out by using a hydroxypropyl cellulose solution as a binder solution.

10. The process according to claim 5, wherein the pharmaceutically acceptable excipient of step (b) comprises a disintegrant selected from the group consisting of silicified microcrystalline cellulose, croscarmellose sodium, sodium starch glycolate, and crospovidone; an additive selected from the group consisting of microcrystalline cellulose, lactose, and mannitol; and a lubricant selected from the group consisting of magnesium stearate, calcium stearate, and talc.

11. The process according to claim 5, wherein the hydroxypropyl methylcellulose of step (c) is used in an amount of 0.02 to 0.1 part by weight based on 1 part by weight of the choline alfoscerate.

12. The process according to claim 5, wherein step (c) is carried out by coating the tablet obtained in step (b) with a film coating solution obtained by dissolving hydroxypropyl methylcellulose in a mixed solvent of anhydrous ethanol and methylene chloride.

13. The process according to claim 5, wherein the polyvinyl alcohol of step (d) is used in an amount of 0.02 to 0.2 part by weight based on 1 part by weight of the choline alfoscerate.

14. The process according to claim 5, wherein step (d) is carried out by coating the film coated tablet obtained in step (c) with a film coating solution obtained by dissolving polyvinyl alcohol in water.

15. The process according to claim 11, wherein step (c) is carried out by coating the tablet obtained in step (b) with a film coating solution obtained by dissolving hydroxypropyl methylcellulose in a mixed solvent of anhydrous ethanol and methylene chloride.

16. The process according to claim 13, wherein step (d) is carried out by coating the film coated tablet obtained in step (c) with a film coating solution obtained by dissolving polyvinyl alcohol in water.

\* \* \* \* \*